(12) United States Patent
Sharkey

(10) Patent No.: US 9,498,272 B2
(45) Date of Patent: Nov. 22, 2016

(54) METHODS AND INSTRUMENTS FOR SUBCHONDRAL TREATMENT OF JOINT DEFECTS NEAR PERIPHERAL ARTICULAR SURFACE

(71) Applicant: ZIMMER KNEE CREATIONS, INC., Exton, PA (US)

(72) Inventor: Peter F. Sharkey, Villanova, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 300 days.

(21) Appl. No.: 14/207,961

(22) Filed: Mar. 13, 2014

(65) Prior Publication Data

US 2014/0276845 A1 Sep. 18, 2014

Related U.S. Application Data

(60) Provisional application No. 61/784,924, filed on Mar. 14, 2013.

(51) Int. Cl.
*A61B 17/88* (2006.01)
*A61F 2/46* (2006.01)
*A61B 17/16* (2006.01)

(52) U.S. Cl.
CPC ....... *A61B 17/8833* (2013.01); *A61B 17/1615* (2013.01); *A61B 17/8811* (2013.01); *A61F 2/461* (2013.01)

(58) Field of Classification Search
CPC .................................................. A61B 17/8833
See application file for complete search history.

(56) References Cited

U.S. PATENT DOCUMENTS

| | | | |
|---|---|---|---|
| 8,062,364 B1 | 11/2011 | Sharkey et al. | |
| 2008/0221511 A1* | 9/2008 | McKay | A61L 27/12 604/60 |
| 2011/0125156 A1* | 5/2011 | Sharkey | A61B 17/1764 606/92 |
| 2011/0125157 A1 | 5/2011 | Sharkey et al. | |

* cited by examiner

*Primary Examiner* — Andrew Yang
(74) *Attorney, Agent, or Firm* — Schwegman Lundberg & Woessner, P.A.

(57) ABSTRACT

Disclosed in some embodiments are instruments and associated methods for the subchondral treatment of defects near a peripheral articular surface of a joint.

17 Claims, 3 Drawing Sheets

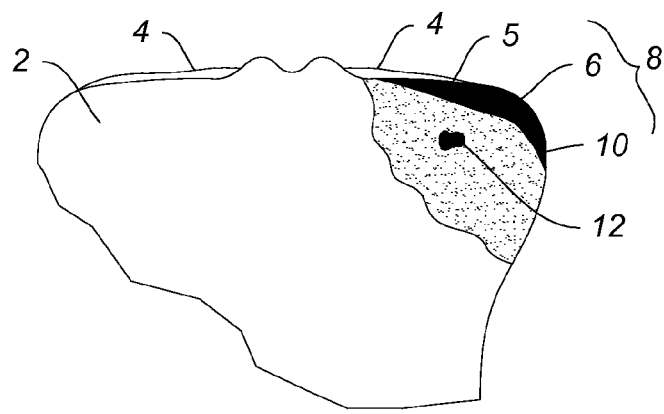
FIG. 1
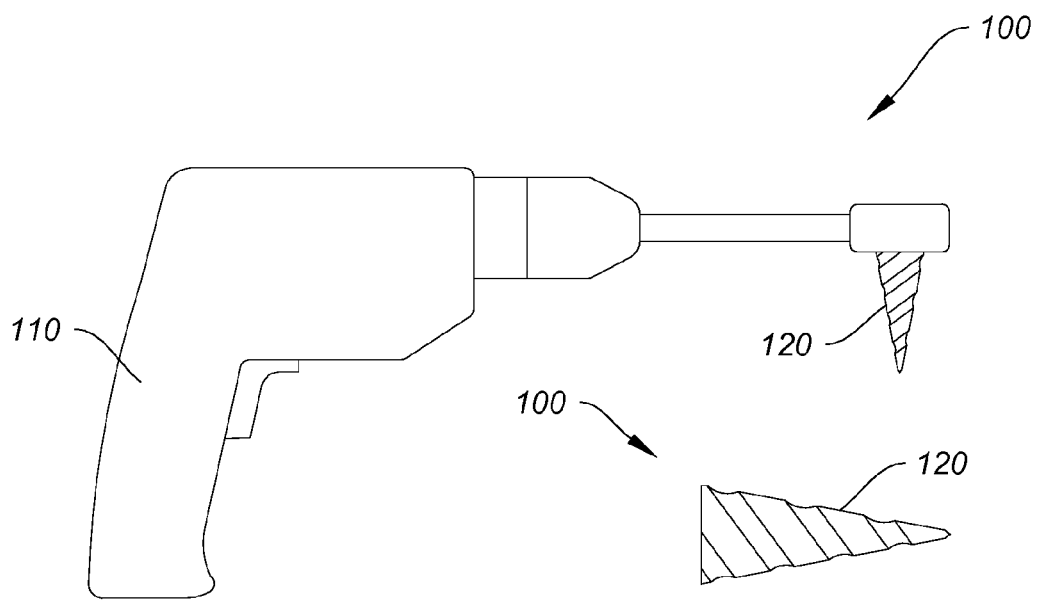
FIG. 2A
FIG. 2B
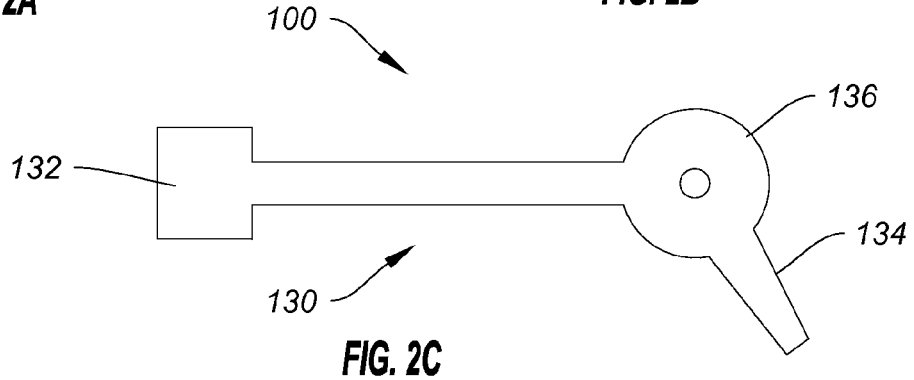
FIG. 2C

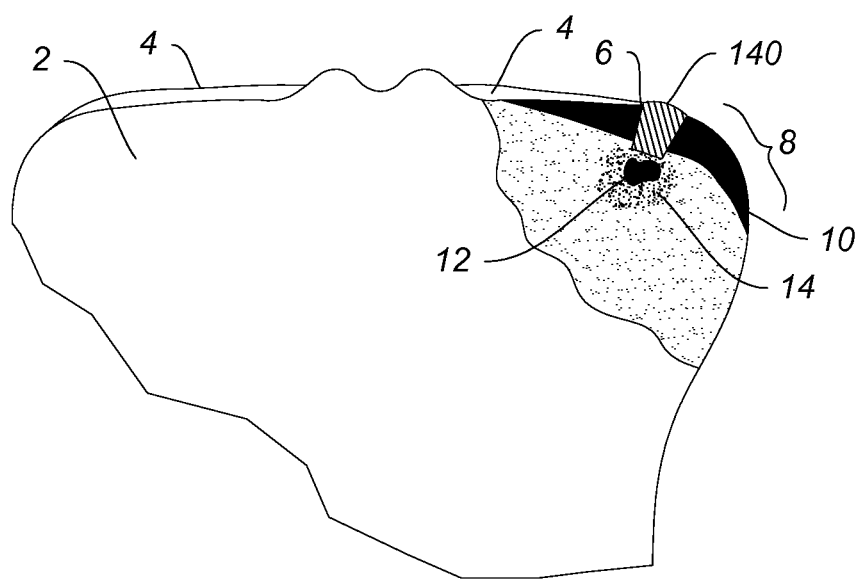
FIG. 5
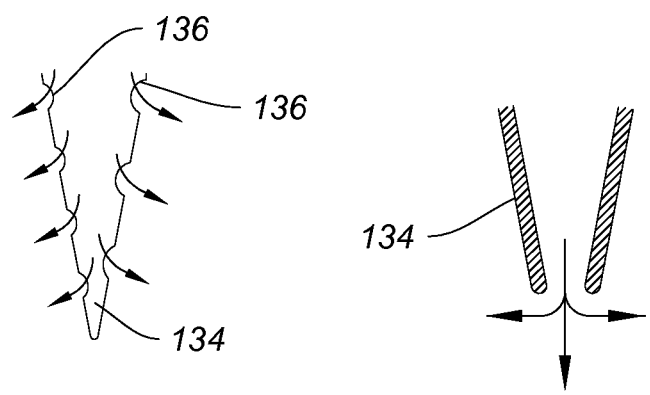
FIG. 6A  FIG. 6B

METHODS AND INSTRUMENTS FOR SUBCHONDRAL TREATMENT OF JOINT DEFECTS NEAR PERIPHERAL ARTICULAR SURFACE

CLAIM OF PRIORITY

This application claims the benefit of U.S. Provisional Patent Application Ser. No. 61/784,924, filed on Mar. 14, 2013, which is incorporated by reference herein in its entirety.

FIELD

The present disclosure relates to methods and instruments for the surgical treatment of joints, and more particularly to methods and instruments for the subchondral repair and treatment of bone tissue at these joints. Even more particularly, the methods repair subchondral defects near the peripheral articular surface of the joint.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in joints such as the knee and ankle, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, microfracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

The technique of subchondrally treating joints affected by osteoarthritis (OA) to relieve the associated pain, as well as treat the underlying disease, has been previously described by applicant. This subchondral treatment involves the stabilization and/or stimulation of the subchondral space at the area of the joint damaged by osteoarthritis, while also preserving as much as possible the articular surface of the joint. This subchondral treatment may be applied to all joints of the human body such as the knee, hip, shoulder, and spine and includes smaller joints such as ankle, elbow, and wrist joints.

In some cases, the ease with which the subchondral treatment developed by applicants is administered depends in large part on the instrumentation that is available to effect the treatment. In the case of subchondral defects that reside near the peripheral articular surface of a joint, precise, controlled and repeatable targeting of the subchondral region of the bone may be particularly challenging due to the inherent natural topography (i.e., curvature) of the bone and the limited area with which to perform the treatment method. Accordingly, it is desirable to provide instruments that can better facilitate treatment in this region of the joint, as well as associated methods.

SUMMARY

The present disclosure provides instruments and associated methods for the surgical repair and treatment of bone tissue, particularly of bone tissue at joints. More specifically, the present disclosure provides instruments and associated methods for the subchondral treatment of defects near a peripheral articular surface of the joint.

In an exemplary embodiment, a method of treating a joint is provided. This particular method includes a step of identifying a subchondral defect in a subchondral region of a bone of a joint where the subchondral defect resides near a peripheral edge of the bone. In another step, access is created to the subchondral region. In another step, bone is augmented, reinforced, stimulated, etc. in and/or adjacent to the subchondral defect via the created access.

In another embodiment, a method of treating a knee joint is provided. This particular method includes a step of identifying a subchondral defect in a subchondral region of a proximal tibia where the subchondral defect extends to less than 5 cm, or less than 4 cm, or less than 3 cm, or less than 2 cm, or less than 1 cm from a peripheral edge of the proximal tibia. In another step, access is created to the subchondral region through an articular surface of the proximal tibia. This creating step avoids passing through cartilage. In another step, an injectable and/or non-injectable material is placed in and/or adjacent to the subchondral defect via the created access.

In one embodiment, a method for treating joint pain is provided. The method may comprise: identifying a subchondral defect in a subchondral region of a bone of a joint, the subchondral defect residing near a peripheral edge of the bone; creating access to the subchondral region near the subchondral defect; and treating the subchondral defect, via the created access; wherein the subchondral defect may be treated by augmenting the bone tissue in the subchondral region near the subchondral defect.

In an exemplary embodiment, creating access comprises drilling a hole to the subchondral region. The access may be created in a transitional zone characterized by the absence of cartilage and presence of cortical bone near the peripheral edge of the bone. The hole may be drilled at an angle. The method may further include the step of sealing the drilled hole, such as by using a plug. In another exemplary embodiment, treating the subchondral defect comprises injecting in the bone, via the created access, a bone hardening material. The bone hardening material may comprise a bone cement, bone void filler, or bone substitute material.

In another embodiment, an instrument kit for treating joint pain is provided. The kit may comprise a power tool having a beveled drill bit attached thereto; a cannula for delivering an injectable material, the cannula having a main body, an end configured for attachment to an injection system, and a delivery end, the delivery end being angled with respect to the main body of the cannula; and a sealing plug.

In an exemplary embodiment, the delivery end is an open end. In still another exemplary embodiment, the delivery end is a closed end. In yet another exemplary embodiment, the delivery end can be angled at about 90, 70, or 60 degrees relative to the main body. Still in other embodiments the delivery end may include side fenestrations or indication markers to show the direction and/or angle at which the delivery end is lying. In a further exemplary embodiment, the sealing plug can comprise allograft or osteochondral material.

As can be seen, the geometries of the associated tools for creating the injection hole (i.e., drill bit, cannula end) as well as the plug, are complementary/matched to create a good, tight fit each step of the process. In order to create an even better seal, it is contemplated that the surgeon could tap the bone to create a threaded injection hole, such that the plug would form an even tighter seal and lock onto the threads within the tapped injection hole.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1 illustrates a cutaway view of a knee joint with a subchondral bone defect near a peripheral articular surface of the joint.

FIGS. 2A-2C show an instrument kit comprising tools for accessing the subchondral bone defect of FIG. 1.

FIGS. 3-5 illustrate steps in a method to access and treat the subchondral bone defect of FIG. 1 using the tools of the instrument kit of FIG. 2.

FIGS. 6A and 6B show enlarged views of exemplary cannula delivery tips of the instrument kit of FIG. 2.

DESCRIPTION OF THE EMBODIMENTS

Figure 3:
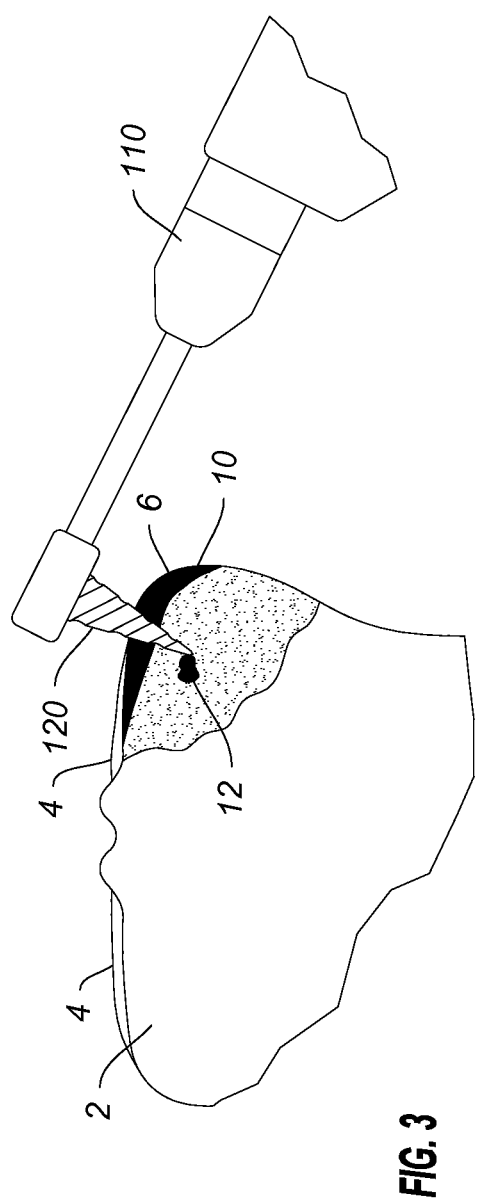

The present disclosure provides instruments and associated methods for the surgical repair and treatment of bone tissue, particularly of bone tissue at joints. More specifically, the present disclosure provides instruments and associated methods for the subchondral treatment of defects near a peripheral articular surface of the joint.

Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Methods, devices and instruments for treating joint pain to restore natural joint function and preserving, as much as possible, the joint's articular and cartilage surface are known. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In an SCP™ procedure, bone fractures or non-unions are stabilized, integrated or healed, which results in reduction of a bone defect, such as a bone marrow lesion or edema. In addition, the SCP™ procedure restores or alters the distribution of forces in a joint to thereby relieve pain. The SCP™ procedure can be performed arthroscopically or percutaneously to treat pain by stabilizing chronic stress fracture, resolving any chronic bone marrow lesion or edema, and preserving, as much as possible, the articular surfaces of the joint. The SUBCHONDROPLASTY™ procedure generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for the SCP™ procedure for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

Various surgical treatments to address subchondral defects known as bone marrow lesions have previously been attempted. Between May and November 2008, three (3) surgeries were performed at Riddle Hospital in Media, Pa. in the United States. On May 12, 2008, Dr. Peter F. Sharkey performed a right knee arthroscopy with arthroscopically assisted stabilization of a patient's right knee with a medial tibial plateau fracture. During the procedure, a cannulated bone biopsy needle was placed into the bone under fluoroscopic guidance, and augmentation material was injected. The injected augmentation material was Stryker Orthopedics Hydroset (Bone Substitute Material). The surgeon expressed difficulty in injecting the bone substitute material.

On Oct. 27, 2008, Dr. Steven B. Cohen performed a left knee arthroscopy, partial medial meniscectomy, drilling of osteochondral lesion using retrograde technique, and debridement chondroplasty of patellofemoral chondrosis on a patient's left knee with medial meniscus tear and left knee osteochondral defect with bone marrow lesion of the medial femoral condyle. During the procedure, an Anterior Cruciate Ligament (ACL) portal-creation device was repurposed for this surgery. The tibial probe was placed on the medial femoral condyle, with the tunnel guide secured proximally on the thigh. The surgeon expressed difficulty in positioning and stabilizing the guide. A cannulated pin was placed through the tunnel guide and placed distally into the medial femoral condyle. No implantable material was injected into the bone in this case.

On Nov. 10, 2008, Dr. Steven B. Cohen performed a right knee arthroscopic-assisted repair of a tibial plateau fracture bone marrow lesion with subchondral fracture using bone cement, partial medial and partial lateral meniscectomy to treat medial meniscus tear, and arthroscopic debridement and chondroplasty of medial, lateral, and patellofemoral compartments to treat compartment chondrosis. During the procedure, a guide pin was inserted into the medial tibial plateau, and an endo button drill bit was used to expand the drill hole. One (1) cubic centimeter (cc) of cement was inserted into the bone. A second drill hole was made from below, and a second cubic centimeter (cc) of cement was inserted into the bone.

The experiences gained from these previous surgeries helped to develop the fundamental theories underlying the SUBCHONDROPLASTY™ procedure and the number of treatment modalities, associated devices, instruments and related methods of use for performing the SUBCHONDROPLASTY™ procedure, which are disclosed in the aforementioned publications. These treatment modalities may be used alone or in combination, as will be described in detail below. In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are known. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

As previously mentioned, bone defects at the edge near the articular surface of periphery of a joint may be often considered eligible for SCP™ treatment due to edge-loading effects as well as the likelihood of bone hardening at these locations. A number of bone marrow lesions or edema (BML or BME) are medial and exist along the peripheral articular surface, such as in knee joints. Since there are higher forces acting on the articular surface at the periphery of the joint (bigger moment arm), BMEs/BMLs can frequently occur subchondrally in this region. The methods and instruments provided herein are described in reference to a knee joint. However, the principles of the present disclosure may be applied just as equally to other bone joints as identified above.

As shown in FIG. 1, in a diseased knee these lesions or edema may reside subchondrally near the peripheral edge of the joint at an area that can be characterized as a transitional zone or "TZ". This transitional zone is loaded under abnormal circumstances, such as where the joint has suffered from structural damage due to osteoarthritis. The transitional zone is loaded in a pathologic joint, or in one that is under more vigorous stress. Often, the transitional zone includes lost cartilage at the articular surface. The transitional zone may extend from the edge of the cartilage surface and sclerotic bone to the peripheral edge of the bone, as identified in FIG. 1.

As seen in FIG. 1, the transitional zone 10 in the tibia 2 may be characterized by the presence of sclerotic bone 6 replacing lost cartilage at its surface. In diseased bone, often the meniscus is torn or degenerated, and pulled back from the peripheral edge 8 of the bone 2. At the same time, the natural cartilage 4 curves a little over the edge 8 of the bone 2. In the case of a joint to be treated with the present method, the transitional zone 10 of the bone can be characterized by a bald spot that is representative of sclerotic bone 6 having replaced lost cartilage, or the junction between the cartilage surface and cortical bone. This bald spot is typically in the center of the crescent-shaped peripheral edge 8 of the bone 2.

The methods of the present disclosure aim to treat the defect in the subchondral region within this transitional zone 10 using the principles of SUBCHONDROPLASTY™ discussed above. The instruments provided herein allow access to the subchondral defect (whether lesion or edema, fracture, fissure, etc.) from the articular surface, and augmentation of the bone tissue around the subchondral defect.

FIGS. 2A-2C show an exemplary embodiment of an instrument kit 100 of the present disclosure. The instrument kit 100 may comprise a drill gun 110 or other power tool, as shown in FIG. 2A. A beveled drill bit 120 similar to the one shown in FIG. 2B can be attached to the power tool 110. The drill gun and beveled drill bit may be used to drill a hole into the bone 2 to treat the defect at the TZ. During use, the beveled surface of the drill bit 110 would provide a good seal with the injection site during injection of material. Other sealing mechanisms may also be employed for the purpose of preventing extrusion during injection.

As shown in FIG. 2C, another instrument in the kit 100 may be an injection cannula 130. The injection cannula 130 may have an end 132 that is configured for attachment to a syringe or injection system for delivering an injectable material, such as a bone hardening material like bone cement, bone void filler, or bone substitute material, consistent with the principles described above with respect to SUBCHONDROPLASTY™ techniques. The delivery end or tip 134 of the injection cannula 130 may be beveled to provide a seal upon insertion into the drilled hole of the bone. In addition, the delivery end 134 may be angled to allow easy access to the subchondral region of the transitional zone 10. In some embodiments, the delivery tip may be pre-bent in a fixed angle, such as at a 90, 75, 60, or other degree angle. In other embodiments, the delivery end 134 of the injection cannula may be angularly adjustable to allow greater flexibility to the user. For example, the delivery tip 134 may be connected to an angularly adjustable neck 136, as shown.

Figure 4:
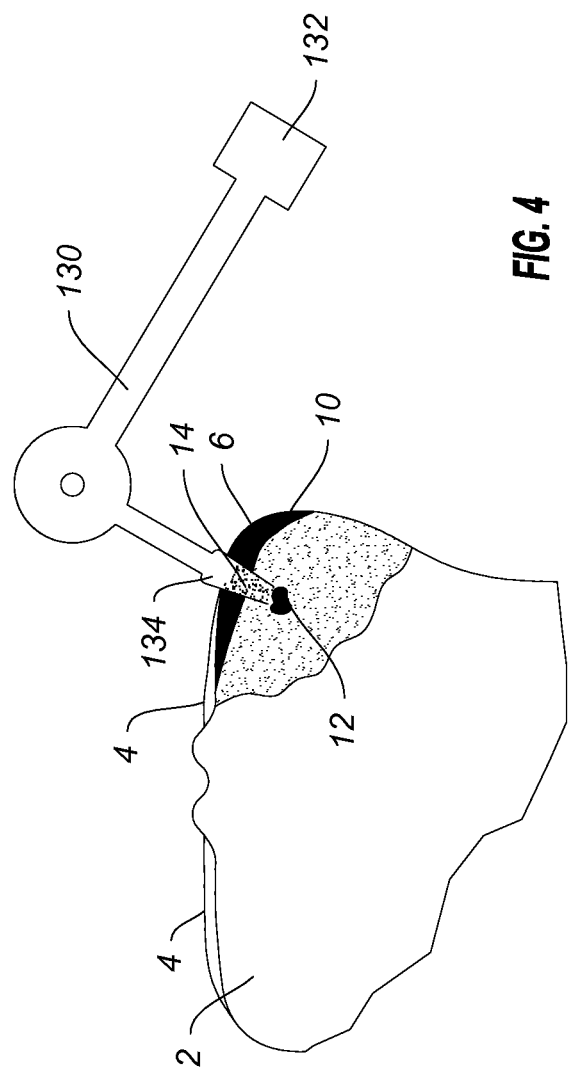

FIGS. 3 to 5 illustrate an exemplary method of the present disclosure. As shown in FIG. 3, the power tool 110 with beveled drill bit 120 may be used to drill a hole in this transitional zone 10 through the articular surface 5 of the bone 2. The drill needs to penetrate hard, sclerotic bone 6 and be able to drill deep enough to access the subchondral region where the defect 12 resides. In practice, drilling should only occur through the sclerotic bone 6 and not through normal healthy cartilage, even if the cartilage is near the transitional zone 10. This is to ensure that you are drilling in a region that is peripheral enough that it is not load-bearing. Load-bearing surfaces should be preserved in their native state as much as possible.

Since the joint gap near this transitional zone 10 is narrow, it is especially important that these instruments within this kit 100 be configured to allow drilling while the bulk of the instruments remains on the outside of the joint. Equally important is the ability to reach below the articular surface and have a length sufficient to reach the subchondral level of the bone 2. In most cases, the hole should be drilled at an angle to go underneath the crescent-shaped peripheral edge 8 of the bone, as shown. Drilling should occur at an angle such as at about 90 degrees, though drilling at other degrees such as about 75 degrees or 60 degrees is also possible. Parallel drilling should be avoided to prevent skiving off the bone 2.

As shown in FIG. 4, after a hole is drilled from the articular surface 5 through to the defect 12 within the subchondral region, the power tool 110 with drill bit 120 may be removed. The injection cannula 130 may then be inserted into the drilled hole. The cannula 130 may be attached to a syringe or other injection system for injection of material such as a bone hardening material or bone substitute material consistent with the principles of SUBCHONDRPLASTY™ treatment. Then, the bone hardening material or bone substitute material 14 may be injected around the subchondral region near the defect 12. This injection may occur right at the junction of the cartilage surface and cortical bone, which is near the edge of the articular surface for peripheral lesions.

Since bone substitute material could extrude back into the joint due to the high pressure being exerted to get it inside the drilled hole, a plug 140 may be provided with the instrument kit 100 to plug or seal up the drilled hole after the injection is complete. As shown in FIG. 5, this plug 140 may comprise a beveled plug formed of allograft or osteochondral material. In addition to sealing the hole to prevent extrusion of material, the plug 140 could also serve the dual function of facilitating cartilage restoration.

As shown in FIG. 6B, the delivery tip 134 of the cannula 130 may be open. In another embodiment, the delivery tip 134 of the cannula 130 may be closed. In addition, the tip 134 may comprise more than one opening for dispensing the material. In one embodiment, as shown in FIG. 6A, the delivery tip may be closed, with one or more ports along the length of the tip for releasing material around the sides of the tip. Varying the configuration of the ports 136 would allow the user to also customize the direction of flow of the material into the subchondral region, as desired. Still in other embodiments, the tip 134 may include side fenestrations, and indication markers in order to let the user know which direction the tip is pointing and/or the angle at which the tip 134 is pointing.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A method of treating a joint, comprising:
identifying a subchondral defect in a subchondral region of a bone of a joint, the subchondral defect residing near a peripheral edge of the bone;
creating access to the subchondral region, wherein the access passes through an articular surface of the bone, and wherein the access passes through sclerotic bone; and
augmenting bone in and/or adjacent to the subchondral defect via the created access.

2. The method of claim 1, wherein the access avoids passing through cartilage.

3. The method of claim 1, wherein the subchondral defect is in a subchondral region of a proximal tibia, the subchondral defect extending to less than 3 cm from a peripheral edge of the proximal tibia, and wherein said creating access to the subchondral region includes passing through an articular surface of the proximal tibia but does not include passing through any cartilage of the proximal tibia, and wherein said augmenting includes injecting an injectable material in and/or adjacent to the subchondral defect via the created access.

4. The method of claim 3, wherein said creating access forms a passage that extends through the articular surface of the proximal tibia and which extends within 15 degrees of perpendicular to the articular surface of the proximal tibia at a point where said passage enters the articular surface of the proximal tibia.

5. The method of claim 3, wherein the access passes through sclerotic bone.

6. A method of treating a joint, comprising:
identifying a subchondral defect in a subchondral region of a bone of a joint, the subchondral defect residing near a peripheral edge of the bone, the bone having an articular surface at the joint that includes articular cartilage;
creating an access path to the subchondral region, wherein the access path passes through an area of the articular surface of the bone that has lost cartilage so that the access path does not pass through any articular cartilage of the articular surface; and
augmenting bone in and/or adjacent to the subchondral defect via the created access path.

7. The method of claim 6, wherein said creating an access path includes drilling a passage into the subchondral defect.

8. The method of claim 6, wherein said creating an access path includes drilling a passage into a subchondral area outside but adjacent to the subchondral defect.

9. The method of claim 6, wherein the subchondral defect extends to less than 1 cm from the peripheral edge of the bone.

10. The method of claim 6, wherein the subchondral defect extends to less than 2 cm from the peripheral edge of the bone.

11. The method of claim 6, wherein the subchondral defect extends to less than 4 cm from the peripheral edge of the bone.

12. The method of claim 6, wherein said augmenting augments bone up to 5 cm from the subchondral defect.

13. The method of claim 6, wherein the subchondral defect is in a subchondral region of a proximal tibia.

14. The method of claim 6, wherein said creating an access path forms a passage that extends through the articular surface of the bone and which extends within 20 degrees of perpendicular to the articular surface of the bone at a point where said passage enters the articular surface.

15. The method of claim 14, wherein said passage extends within 5 degrees of perpendicular to the articular surface of the bone at a point where said passage enters the articular surface.

16. The method of claim 6, wherein said augmenting includes injecting an injectable material into the subchondral defect.

17. The method of claim 6, wherein the access path passes through sclerotic bone.

\* \* \* \* \*